(12) United States Patent
Wierzbicki et al.

(10) Patent No.: US 6,465,660 B1
(45) Date of Patent: Oct. 15, 2002

(54) ISOINDOLOINDOLONE COMPOUNDS

(75) Inventors: Michel Wierzbicki, L'Etang la Ville; Marie-Françoise Boussard, Mareil sur Mauldre; Anne Rousseau, Longjumeau; Jean Albert Boutin, Suresnes; Philippe Delagrange, Issy les Moulineaux, all of (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 10/083,074

(22) Filed: Feb. 26, 2002

(30) Foreign Application Priority Data

Mar. 12, 2001 (FR) .............................. 0103293

(51) Int. Cl.⁷ .................. C07D 209/58; A61K 31/4035
(52) U.S. Cl. ...................................... 548/420
(58) Field of Search ........................ 548/420; 514/410

(56) References Cited

FOREIGN PATENT DOCUMENTS

WO          WO 02/00215      *   1/2002

OTHER PUBLICATIONS

Black DS, Keller PA, Kumar N. Synthesis of pyrrolophenanthridones by aryl–aryl coupling reactions. Tetrahedron 1993;49:151–64.*

* cited by examiner

Primary Examiner—Joseph K. McKane
Assistant Examiner—Jennifer C. Murphy
(74) Attorney, Agent, or Firm—The Firm of Hueschen and Sage

(57) ABSTRACT

Compound of formula (I):

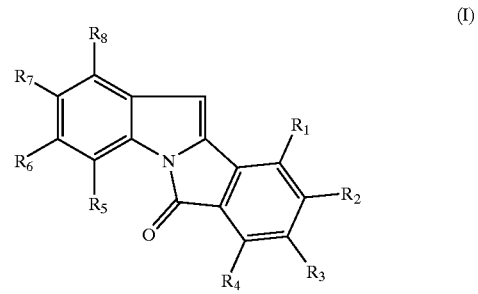

wherein:

$R_1$, $R_2$, $R_3$, $R_4$, $R_5$, $R_6$ and $R_8$, which may be identical or different, each represents hydrogen, alkyl, arylalkyl, hydroxy, alkoxy, arylalkoxy, acyloxy, arylcarbonyloxy, carboxyalkyl or carboxy, $R_7$ represents hydrogen, hydroxy, alkoxy, arylalkoxy, acyloxy or arylcarbonyloxy group, or one of $R_1$ to $R_8$, together with another of $R_1$ to $R_8$ adjacent to it, forms an alkylenedioxy, its optical isomers, and addition salts thereof with a pharmaceutically acceptable acid or base.

4 Claims, No Drawings

ISOINDOLOINDOLONE COMPOUNDS

DESCRIPTION OF THE PRIOR ART

A number of isoindoloindolone compounds have been described in the literature, especially in Tetrahedron 1993, 49 (1), 151–164, without any pharmacological activity being described for those compounds.

The compounds of the present invention are new and exhibit pharmacological characteristics that are very valuable in respect of melatoninergic receptors.

BACKGROUND OF THE INVENTION

Numerous studies in the last ten years have demonstrated the key role of melatonin (N-acetyl-5-methoxytryptamine) in many physiopathological phenomena and in the control of circadian rhythm, but melatonin has a rather short half-life owing to the fact that it is rapidly metabolised. Great interest therefore lies in the possibility of making available to the clinician melatonin analogues that are metabolically more stable and have an agonist or antagonist character and of which the therapeutic effect may be expected to be superior to that of the hormone itself.

In addition to their beneficial action in respect of circadian rhythm disorders (J. Neurosurg. 1985, 63, pp. 321–341) and sleep disorders (Psychopharmacology, 1990, 100, pp. 222–226), ligands of the melatoninergic system have valuable pharmacological properties in respect of the central nervous system, especially anxiolytic and antipsychotic properties (Neuropharmacology of Pineal Secretions, 1990, 8 (3–4), pp. 264–272), and analgesic properties (Pharmacopsychiat., 1987, 20, pp. 222–223), and also for the treatment of Parkinson's disease (J. Neurosurg. 1985, 63, pp. 321–341) and Alzheimer's disease (Brain Research, 1990, 528, pp. 170–174). The compounds have also demonstrated activity in relation to certain cancers (Melatonin—Clinical Perspectives, Oxford University Press, 1988, pp. 164–165), ovulation (Science 1987, 227, pp. 714–720), diabetes (Clinical Endocrinology, 1986, 24, pp. 359–364), and in the treatment of obesity (International Journal of Eating Disorders, 1996, 20 (4), pp. 443–446).

Those various effects are exerted via the intermediary of specific melatonin receptors. Molecular biology studies have demonstrated the existence of a number of receptor subtypes that are capable of binding that hormone (Trends Pharmacol. Sci., 1995, 16, p. 50; WO 97 04094). It has been possible for some of those receptors to be located and characterised for different species, including mammals. In order to be able to understand the physiological functions of those receptors better, it is of great advantage to have available specific ligands. Moreover such compounds, by interacting selectively with one or another of those receptors, may be excellent medicaments for the clinician in the treatment of pathologies associated with the melatoninergic system, some of which have been mentioned above.

The compounds of the present invention, in addition to being new, exhibit a strong affinity for melatonin receptors and a significant selectivity for sites of the $MT_3$ type.

DETAILED DESCRIPTION OF THE INVENTION

The present invention relates more especially to the compounds of formula (I)

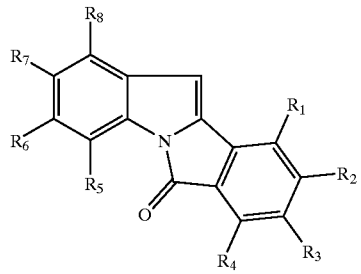

wherein $R_1$, $R_2$, $R_3$, $R_4$, $R_5$, $R_6$ and $R_8$, which may be identical or different, each represents a hydrogen atom or a linear or branched ($C_1$–$C_6$)alkyl group, an aryl-($C_1$–$C_6$)alkyl group in which alkyl may be linear or branched, a hydroxy group, a linear or branched ($C_1$–$C_6$)alkoxy group, an aryl-($C_1$–$C_6$)alkoxy group in which alkoxy may be linear or branched, a linear or branched ($C_1$–$C_6$) acyloxy group, an arylcarbonyloxy group, a carboxy-($C_1$–$C_6$)alkyl group in which alkyl may be linear or branched, or a carboxy group, $R_7$ represents a hydrogen atom or a hydroxy group, a linear or branched ($C_1$–$C_6$)alkoxy group, an aryl-($C_1$–$C_6$)alkoxy group in which alkoxy may be linear or branched, a linear or branched ($C_1$–$C_6$)acyloxy group or an arylcarbonyloxy group, or one of the groups $R_1$ to $R_8$, together with another of the groups $R_1$ to $R_8$ adjacent to it, forms a ($C_1$–$C_2$) alkylenedioxy group, to their optical isomers, where they exist, and to addition salts thereof with a pharmaceutically acceptable acid or base, with the proviso:

that at least one of the groups $R_1$ to $R_8$ represents a hydroxy, a linear or branched ($C_1$–$C_6$)alkoxy, a linear or branched ($C_1$–$C_6$)acyloxy or an arylcarbonyloxy group, and that the compounds of formula (I) are other than 1,3-dimethoxy-6H-isoindolo[2,1-a]indol-6-one.

"Aryl" is to be understood as phenyl, biphenyl, naphthyl or tetrahydronaphthyl, wherein each of those groups is optionally substituted by one or more identical or different atoms or groups selected from halogen atoms and linear or branched ($C_1$–$C_6$)alkyl, hydroxy, linear or branched ($C_1$–$C_6$) alkoxy, linear or branched ($C_1$–$C_6$)polyhaloalkyl, amino (optionally substituted by one or more linear or branched ($C_1$–$C_6$)alkyl groups), nitro, linear or branched ($C_1$–$C_6$)acyl and ($C_1$–$C_2$)alkylenedioxy.

Amongst the pharmaceutically acceptable acids there may be mentioned, without implying any limitation, hydrochloric, hydrobromic, sulphuric, phosphoric, acetic, trifluoroacetic, lactic, pyruvic, malonic, succinic, glutaric, fumaric, tartaric, maleic, citric, ascorbic, methanesulphonic, camphoric, oxalic acid.

Amongst the pharmaceutically acceptable bases there may be mentioned, without implying any limitation, sodium hydroxide, potassium hydroxide, triethylamine, tert-butylamine.

The invention relates also to a process for the preparation of the compounds of formula (I) which is characterised in that a compound of formula (II):

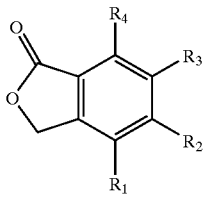

wherein $R_1$, $R_2$, $R_3$ and $R_4$ are as defined for formula (I), is reacted with N-bromosuccinimide to yield a compound of formula (III):

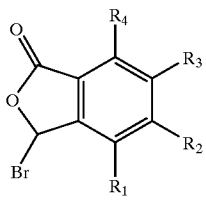

wherein $R_1$, $R_2$, $R_3$ and $R_4$ are as defined hereinbefore, which is reacted with triphenylphosphine to yield a compound of formula (IV):

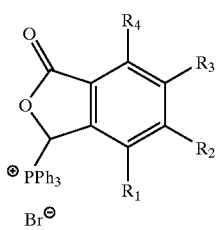

wherein $R_1$, $R_2$, $R_3$ and $R_4$ are as defined hereinbefore, which is reacted with a compound of formula (V):

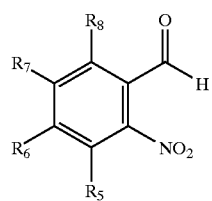

wherein $R_5$, $R_6$, $R_7$ and $R_8$ are as defined for formula (I), to yield a compound of formula (VI):

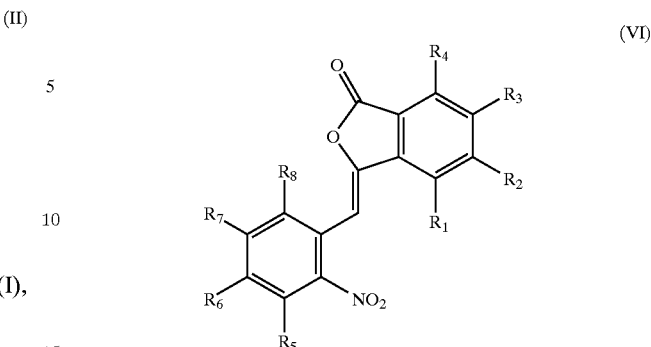

wherein $R_1$, $R_2$, $R_3$, $R_4$, $R_5$, $R_6$, $R_7$ and $R_8$ are as defined hereinbefore, which is subjected to the action of a reducing agent to yield a compound of formula (VII):

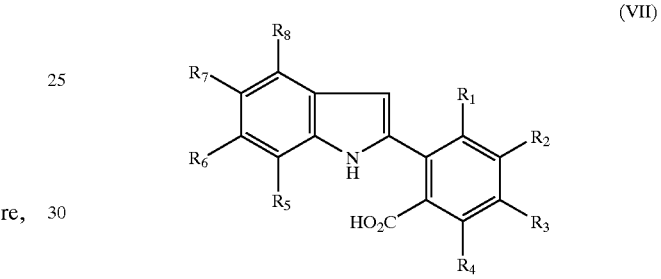

wherein $R_1$, $R_2$, $R_3$, $R_4$, $R_5$, $R_6$, $R_7$ and $R_8$ are as defined hereinbefore, which is then cyclised to yield a compound of formula (I), which is purified, if necessary, according to a conventional purification technique, is separated, if desired, into its optical isomers according to a conventional separation technique, and is converted, if desired, into addition salts with a pharmaceutically acceptable acid or base.

The compounds of the invention and the pharmaceutical compositions containing them have proved useful in the treatment of disorders of the melatoninergic system.

A pharmacological study of the compounds of the invention has in fact demonstrated that they are non-toxic, have a high selective affinity for melatonin receptors and have substantial activity in respect of the central nervous system and, in particular, they have been found to have therapeutic properties in respect of sleep disorders, anxiolytic, antipsychotic and analgesic properties and properties in respect of microcirculation, enabling it to be established that the compounds of the invention are useful in the treatment of stress, sleep disorders, anxiety, seasonal affective disorders, cardiovascular pathologies, pathologies of the digestive system, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory losses, Alzheimer's disease, and in cerebral circulation disorders. In another field of activity, it appears that the compounds of the invention can be used in the treatment of sexual dysfunctions, that they have ovulation-inhibiting and immunomodulating properties and that they are capable of being used in the treatment of cancers.

The compounds will preferably be used in the treatment of seasonal affective disorders, sleep disorders, cardiovascular pathologies, insomnia and fatigue due to jetlag, appetite disorders and obesity.

For example, the compounds will be used in the treatment of seasonal affective disorders and sleep disorders.

The present invention relates also to pharmaceutical compositions comprising a compound of formula (I) in combination with one or more pharmaceutically acceptable excipients.

Amongst the pharmaceutical compositions according to the invention there may be mentioned more especially those which are suitable for oral, parenteral, nasal, per- or transcutaneous, rectal, perlingual, ocular or respiratory administration, especially tablets or dragees, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication or possibly associated treatments, and ranges from 0.01 mg to 1 g per 24 hours in one or more administrations.

The following Examples illustrate the invention but do not limit it in any way.

The starting materials used are known products or products prepared according to known preparation procedures.

The structures of the compounds described in the Examples were determined according to customary spectrometric techniques (infra-red, NMR, mass spectrometry).

EXAMPLE 1

2-Hydroxy-8,9-dimethoxyisoindolo[2,1-a]indol-6-one

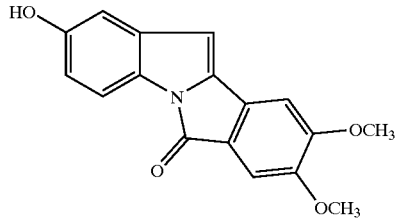

Step A: 3-Bromo-5,6-dimethoxyphthalide 12 mmol of N-bromosuccinimide are added to 10 mmol of 5,6-dimethoxyphthalide dissolved in dichloromethane and then the reaction mixture, illuminated with a halogen lamp, is heated at reflux for 5 hours. The mixture is then brought to ambient temperature and filtered, and the filtrate is subsequently evaporated, toluene is added, the suspension obtained is filtered and the filtrate is evaporated. The residue obtained is filtered through silica to yield the expected product.

Step B: (5,6-Dimethoxyphthalidyl)triphenylphosphonium bromide 10 mmol of triphenylphosphine are added to 10 mmol of the compound obtained in the above Step in solution in toluene and then the reaction mixture is heated at reflux for 3 hours. After returning to ambient temperature, the mixture is filtered and the cake obtained is then washed and dried to yield the expected product.

Melting point:>260° C.

Step C: 3-(5-Hydroxy-2-nitrobenzylidene)-5,6-dimethoxyphthalide 10 mmol of triethylamine and then, in portions, 10 mmol of the compound obtained in the above Step, are added to 10 mmol of 5-hydroxy-2-nitrobenzaldehyde dissolved in dimethylformamide. The reaction mixture is then heated at 50° C. for 1 hour 30 minutes and subsequently brought to ambient temperature and evaporated. Ether is then added and the mixture is stirred for one night and then filtered. The cake obtained is subsequently washed to yield the expected product.

Melting point: 253° C.

Step D: 3-(2-Amino-5-hydroxybenzylidene)-5,6-dimethoxyphthalide

A solution of the compound described in the above Step (10 mmol) in dimethylformamide is placed under hydrogen in the presence of Raney nickel until 34 mmol of hydrogen have been absorbed. After removal of the catalyst by filtration, the solvent is evaporated off and the residue is dried to yield the expected product.

Melting point: 231° C.

Step E: 2-(2-Carboxy-4,5-dimethoxyphenyl)-5-hydroxyindole 20 mmol of aqueous 1N sodium hydroxide solution are added to 10 mmol of the compound described in the above Step in solution in ethanol, and then the mixture is heated at reflux for three quarters of an hour. After cooling to 0° C., the mixture is adjusted to a pH of 1 using 1N hydrochloric acid and then, after 1 hour at ambient temperature, the precipitate that has formed is filtered off and subsequently washed and dried to yield the expected product.

Melting point: 160° C.

Step F: 2-Hydroxy-8,9-dimethoxyisoindolo[2,1-a]indol-6-one 10 mmol of the compound obtained in the above Step, in solution in toluene, and then 0.15 mmol of para-toluenesulphonic acid, are introduced into a flask fitted with a Dean-Stark apparatus. After one night at reflux, the reaction mixture is brought to ambient temperature and then filtered. The cake is subsequently washed and then tetrahydrofuran is added, the suspension is filtered, the filtrate obtained is evaporated and the residue is washed and then dried to yield the expected product.

Melting point:>260° C.

| Elemental microanalysis: | | | |
|---|---|---|---|
| | C% | H% | N% |
| calculated | 69.15 | 4.44 | 4.74 |
| found | 69.05 | 4.18 | 4.98 |

EXAMPLE 2

2-Hydroxy-10-methoxyisoindolo[2,1-a]indol-6-one

The expected product is obtained in accordance with the procedure described in Example 1, starting from 4-methoxyphthalide and 5-hydroxy-2-nitrobenzaldehyde.

Melting point: 250° C.

| Elemental microanalysis: | | | |
|---|---|---|---|
| | C% | H% | N% |
| calculated | 72.45 | 4.18 | 5.28 |
| found | 72.14 | 4.31 | 5.28 |

EXAMPLE 3

2-Hydroxy-7,10-dimethoxyisoindolo[2,1-a]indol-6-one

The expected product is obtained in accordance with the procedure described in Example 1, starting from 4,7-dimethoxyphthalide and 5-hydroxy-2-nitrobenzaldehyde.

Melting point:>260° C.

Elemental microanalysis:

|  | C% | H% | N% |
|---|---|---|---|
| calculated | 69.15 | 4.44 | 4.74 |
| found | 68.80 | 4.52 | 4.81 |

EXAMPLE 4

2-Hydroxy-8-methoxyisoindolo[2,1-a]indol-6-one

The expected product is obtained in accordance with the procedure described in Example 1, starting from 6-methoxyphthalide and 5-hydroxy-2-nitrobenzaldehyde.

Melting point: 217° C.

Elemental microanalysis:

|  | C% | H% | N% |
|---|---|---|---|
| calculated | 72.45 | 4.18 | 5.28 |
| found | 72.10 | 4.51 | 5.06 |

EXAMPLE 5

2,9-Dihydroxy-8-methoxyisoindolo[2,1-a]indol-6-one

The expected product is obtained in accordance with the procedure described in Example 1, starting from 5-hydroxy-6-methoxyphthalide and 5-hydroxy-2-nitrobenz-aldehyde.

Melting point:>260° C.

EXAMPLE 6

2,8-Dihydroxyisoindolo[2,1 -a]indol-6-one

The expected product is obtained in accordance with the procedure described in Example 1, starting from 6-hydroxyphthalide and 5-hydroxy-2-nitrobenzaldehyde.

Melting point:>260° C.

EXAMPLE 7

8-Hydroxy-2-methoxyisoindolo[2,1-a]indol-6-one

The expected product is obtained in accordance with the procedure described in Example 1, starting from 6-hydroxyphthalide and 5-methoxy-2-nitrobenzaldehyde.

Melting point: 100° C.

EXAMPLE 8

8-Hydroxy-2,3-methylenedioxyisoindolo[2,1-a]indol-6-one

The expected product is obtained in accordance with the procedure described in Example 1, starting from 6-hydroxyphthalide and 4,5-methylenedioxy-2-nitrobenz-aldehyde.

Melting point: 80° C.

EXAMPLE 9

2-Hydroxy-8,10-dimethoxyisoindolo[2,1-a]indol-6-one

The expected product is obtained in accordance with the procedure described in Example 1, starting from 4,6-dimethoxyphthalide and 5-hydroxy-2-nitrobenzaldehyde.

Melting point:>260° C.

Elemental microanalysis:

|  | C% | H% | N% |
|---|---|---|---|
| calculated | 69.15 | 4.44 | 4.74 |
| found | 69.06 | 4.42 | 4.77 |

EXAMPLE 10

3-Benzyl-2-hydroxy-8,10-dimethoxyisoindolo[2,1-a]indol-6-one

The expected product is obtained in accordance with the procedure described in Example 1, starting from 4,6-dimethoxyphthalide and 4-benzyl-5-hydroxy-2-nitrobenzaldehyde.

EXAMPLE 11

2,7-Dihydroxyisoindolo[2,1-a]indol-6-one

The expected product is obtained in accordance with the procedure described in Example 1, starting from 7-hydroxyphthalide and 5-hydroxy-2-nitrobenzaldehyde.

Melting point: 250° C.

EXAMPLE 12

2,7,10-Trihydroxyisoindolo[2,1-a]indol-6-one

The expected product is obtained in accordance with the procedure described in Example 1, starting from 4,7-dihydroxyphthalide and 5-hydroxy-2-nitrobenzaldehyde.

EXAMPLE 13

2,7-Dihydroxy-10-methoxyisoindolo[2,1-a]indol-6-one

The expected product is obtained in accordance with the procedure described in Example 1, starting from 7-hydroxy-4-methoxyphthalide and 5-hydroxy-2-nitrobenz-aldehyde.

EXAMPLE 14

1-Carboxyethyl-8,9-dimethoxyisoindolo[2,1-a]indol-6-one

The expected product is obtained in accordance with the procedure described in Example 1, starting from 5,6-dimethoxyphthalide and 6-carboxyethyl-2-nitrobenz-aldehyde.

EXAMPLE 15

8-Carboxy-7,9-dimethyl-2-hydroxyisoindolo[2,1-a]indol-6-one

The expected product is obtained in accordance with the procedure described in Example 1, starting from 6-carboxy-5,7-dimethylphthalide and 5-hydroxy-2-nitrobenz-aldehyde.

Pharmacological Study of the Compounds of the Invention

EXAMPLE 16

Study of binding to melatonin $MT_3$ binding sites

Binding to $MT_3$ sites is characterised by remarkably rapid association and dissociation kinetics and by tissue localisation (brain).

The experiments of binding to $MT_3$ sites are carried out on hamster brain membranes using $2\text{-}[^{125}I]$ iodomelatonin as radioligand in accordance with the protocol described by P. Paul et al. (J. Pharmacol. Exp. Ther. 1999 290, 334). The membranes are incubated for 30 minutes with $2\text{-}[^{125}I]$ iodomelatonin at a temperature of 4° C. and at different concentrations of the compounds to be tested. Following incubation, the membranes are rapidly filtered and then washed with cold buffer using a filtration system. The radioactivity retained is measured using a scintillation counter.

The $IC_{50}$ values found for the compounds of the invention testify to a strong affinity for sites of the $MT_3$ type, those values being less than 10 nM. By way of comparison, melatonin has an $IC_{50}$ of 45 nM in this test.

EXAMPLE 17

Pharmaceutical Composition

Formulation for the preparation of 1000 tablets each comprising 10 mg of active ingredient compound of Example 1 . . . 10 g hydroxypropyl cellulose . . . 2 g wheat starch . . . 10 g lactose . . . 100 g magnesium stearate . . . 3 g talc . . . 3 g

We claim:
1. A compound selected from those of formula (I):

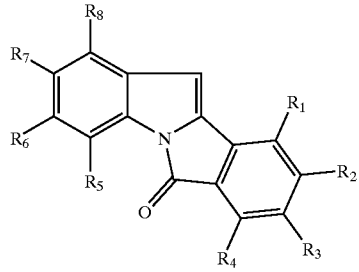

wherein:
$R_1$, $R_2$, $R_3$, $R_4$, $R_5$, $R_6$ and $R_8$, which may be identical or different, each represents hydrogen, linear or branched $(C_1-C_6)$alkyl, aryl-$(C_1-C_6)$alkyl in which alkyl may be linear or branched, hydroxy, linear or branched $(C_1-C_6)$ alkoxy, aryl-$(C_1-C_6)$alkoxy in which alkoxy may be linear or branched, linear or branched $(C_1-C_6)$acyloxy, arylcarbonyloxy, carboxy-$(C_1-C_6)$alkyl in which alkyl may be linear or branched or carboxy, $R_7$ represents hydrogen, hydroxy, linear or branched $(C_1-C_6)$alkoxy, aryl-$(C_1-C_6)$alkoxy in which alkoxy may be linear or branched, linear or branched $(C_1-C_6)$ acyloxy or arylcarbonyloxy, or one of $R_1$ to $R_8$, together with another of $R_1$ to $R_8$ adjacent to it, forms $(C_1-C_2)$alkylenedioxy, optical isomers thereof, where they exist, and addition salts thereof with a pharmaceutically acceptable acid or base, with the proviso:

that at least one of $R_1$ to $R_8$ represents hydroxy, linear or branched $(C_1-C_6)$alkyl, linear or branched $(C_1-C_6)$ acyloxy or arylcarbonyloxy, and that the compounds of formula (I) are other than 1,3-dimethoxy-6H-isoindolo[2,1-a]indol-6-one.

2. The compound of claim 1 which is 2-hydroxy-8,9-dimethoxyisoindolo[2,1-a]indol-6-one.

3. A method for treating a living animal body afflicted with a disorder of the melatoninergic system, comprising the step of administering to the living animal body an effective amount of a compound of claim 1 which is effective for alleviation of said disorder.

4. A pharmaceutical composition useful for treatment of a disorder of the melatoninergic system, comprising as active principle an effective amount of a compound as claimed in claim 1, together with one or more pharmaceutically acceptable, inert, non-toxic excipients or vehicles.

* * * * *